United States Patent [19]

Sundeen et al.

[11] 4,208,415
[45] Jun. 17, 1980

[54] 4-[2-(2-SUBSTITUTED PHENYL)ETHENYL]-N-ALKENYL OR ALKINYL SUBSTITUTED 1,2,3,6-TETRAHYDROPYRIDINES

[75] Inventors: Joseph E. Sundeen, Yardley, Pa.; Frederick P. Hauck, Bridgewater, N.J.

[73] Assignee: E. R. Squibb & Sons, Inc., Princeton, N.J.

[21] Appl. No.: 875,276

[22] Filed: Feb. 6, 1978

[51] Int. Cl.$^2$ .................. A61K 31/44; C07D 211/70
[52] U.S. Cl. ................................... 424/263; 542/455
[58] Field of Search ........................ 542/455; 424/263

[56] References Cited

U.S. PATENT DOCUMENTS

| | | | |
|---|---|---|---|
| 3,898,236 | 8/1975 | Hauck et al. | 260/288 CF |
| 3,953,434 | 4/1976 | Hauck et al. | 542/455 |
| 3,965,102 | 6/1976 | Hauck et al. | 260/286 R |
| 4,016,223 | 4/1977 | Rajadhyaksha et al. | 260/946 |
| 4,038,415 | 7/1977 | Rajadhyaksha et al. | 424/317 |

OTHER PUBLICATIONS

Gauthier, (Ph.D. Thesis, Univ. of New Hampshire, 1966), pp. 116, 117 & 135.
Peskar et al., *J. Pharm. Pharmac.*, 1976, 28, 146.
Anggard et al., Methods in Enzymology, vol. 14, (1969), pp. 215–219.

Primary Examiner—Frederic E. Waddell
Attorney, Agent, or Firm—Lawrence S. Levinson; Stephen B. Davis

[57] ABSTRACT

Compounds of the formula and their pharmaceutically acceptable acid addition salts

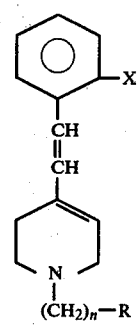

wherein X is lower alkoxy, Cl, Br, or F; R is

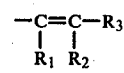

or —C≡C—R$_4$; R$_1$, R$_2$, R$_3$, and R$_4$ are independently selected from hydrogen and methyl; n is an integer from 1 to 3 provided that when n is 3 at least two of R$_1$, R$_2$ and R$_3$ are hydrogen and R$_4$ is hydrogen, and further provided that when n is 2 at least one of R$_1$, R$_2$ and R$_3$ is hydrogen; are disclosed. These compounds possess useful pharmaceutical activities due to their ability to inhibit the prostaglandin-inactivating enzyme 15-α-hydroxyprostaglandin dehydrogenase.

8 Claims, No Drawings

4-[2-(2-SUBSTITUTED PHENYL)ETHENYL]-N-ALKENYL OR ALKINYL SUBSTITUTED 1,2,3,6-TETRAHYDROPYRIDINES

BACKGROUND OF THE INVENTION

Hauck et al. in U.S. Pat. Nos. 3,898,236 and 3,965,102 disclose the preparation of 4-[(substituted phenyl)ethenyl]-N-alkyl or phenyl-lower alkyl substituted 1,2,3,6-tetrahydropyridines. Hauck et al. employ such compounds as intermediates in the preparation of various 2,3,3a,4,6,7,8,9,9a,9b-decahdro-4-(substituted phenyl)-1H-pyrrolo[3,4-h]isoquinolines.

Gautier (Ph.D Thesis, University of New Hampshire, 1966) discloses the preparation of 4-[(phenyl)ethenyl]-N-methyl substituted 1,2,3,6-tetrahydropyridine.

Peskar et al. in the Journal of Pharmacy and Pharmacology, Vol. 28, p. 146–148 (1976) disclose the inhibition of 15-α-hydroxyprostaglandin dehydrogenase by the anti-ulcer agent carbenoxolone.

Rajadhyaksha et al. in U.S. Pat. Nos. 4,016,223 and 4,038,415 discloses various compounds which inhibit prostaglandin dehydrogenase and lower blood pressure and potentiate the cardiovascular effects of exogenous prostaglandins.

SUMMARY OF THE INVENTION

This invention relates to new 4-[2-(2-substituted phenyl)ethenyl]-N-alkenyl or alkinyl substituted 1,2,3,6-tetrahydropyridines and their pharmaceutically acceptable acid addition salts of the formula

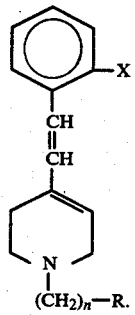

(I)

X is lower alkoxy, Cl, Br, or F.
R is

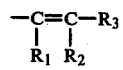

or —C≡C—R$_4$.

R$_1$, R$_2$, R$_3$ and R$_4$ are independently selected from hydrogen and methyl.

n is an integer from 1 to 3, provided that when n is 3 at least two of R$_1$, R$_2$, and R$_3$ are hydrogen and R$_4$ is hydrogen and that when n is 2 at least one of R$_1$, R$_2$ and R$_3$ is hydrogen.

DETAILED DESCRIPTION OF THE INVENTION

The term "lower alkoxy" as used throughout this specification is meant to include straight or branched chain hydrocarbon groups having 1 to 4 carbon atoms linked to an oxygen atom, i.e. methoxy, ethoxy, t-butoxy, etc.

The new compounds of formula I wherein R is

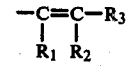

are prepared by reacting a 2-substituted styryl-4-pyridine of formula II

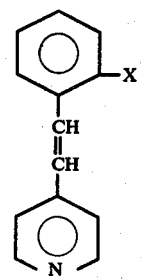

(II)

with an equimolar or molar excess of a halo substituted alkylene of formula III

(III)

wherein halo is Br or Cl and X, n, R$_1$, R$_2$ and R$_3$ are as defined above to yield quaternary compound of formula

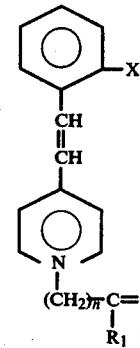

The above reaction is performed in an inert organic solvent such as acetonitrile at abut 20° to about 30° C. for from about 12 to about 72 hours.

The quaternary intermediate of formula IV is then reduced with a chemical reducing agent such as sodium borohydride in methanol to yield the corresponding compound of formula I.

The new compounds of formula I wherein R is —C≡C—R$_4$ are prepared by reacting a 2-substituted styryl-4-(1,2,3,6-tetrahydropyridine) of formula V

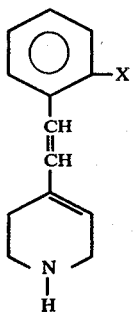

(V)

with about an equimolar amount of a halo substituted alkine of formula VI (VI) halo—$(CH_2)_n$C≡C—$R_4$ wherein halo is Br or Cl and X, n, and $R_4$ are as defined above to yield the corresponding compound of formula I. This reaction is performed in an inert organic solvent such as benzene at a temperature of from about 30° to about 60° for from about 4 to about 24 hours. Preferably, an equimolar amount of triethylamine is included within the reaction mixture.

Also, the alkenyl substituted compounds of formula I can be prepared by reacting the tetrahydropryidine of formula V with the halo substituted alkylene of formula III.

The startng materials of formula II are prepared as taught by Hauck et al. in the patents noted aboe by reacting a 4-methylpyridine with the appropriate 2-substituted benzaldehyde.

The tetrahydropyridine of formula V is prepared by dissolving 1-benzyl-1,2,3,6-tetrahydro-4-(2-substituted styryl)-pyridine of formula VII

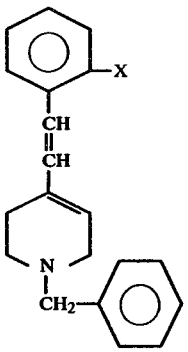

(VII)

in an organic solvent and treating it with trichloroethyl chloroformate. The resulting product is then dissolved in glacial acetic acid and treated with zinc dust to yield the compound of formula V.

Depending on the reaction conditions and the starting materials used, the compounds of formula I are obtained in the free form or in the form of their acid addition salts. The salts thereof can be converted into the free compounds in a known manner such as by reaction with a basic agent. Free bases which may be obtained can be converted into pharmaceutically acceptable acid addition salts by reaction with a variety of acids. Acids useful for preparing these acid-addition salts include, inter alia, inorganic acids, such as the hydrohalic acids (e.g. hydrochloric and hydrobornic acid), sulfuric acid, nitric acid, and phosphoric acid, and organic acids such as maleic, fumaric, tartaric, citric, acetic, benzoic, 2-acetoxybenzoic, salicylic, succinic, nicotinic, methanesulfonic or cyclohexanesulfamic.

Preferred compounds of this invention are those of formula I wherein X is methoxy, ethoxy, Cl, or Br; n is 1 or 2; and $R_1$, $R_2$, $R_3$ and $R_4$ are hydrogen.

Most preferred are those compounds of formula I wherein X is methoxy or Cl; n is 1; and R is

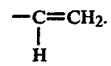

The compounds of this invention including their pharmaceutically acceptable salts have exhibited the ability to inhibit the action of 15-α-hydroxyprostaglandin dehydrogenase assayed according to the general procedure described by Anggard et al. (Methods In Enzymology, Vol. 14, pages 215–219 (1969)). Thus the compounds of this invention are useful pharmaceutical agents possessing the ability to potentiate the pharmacological effects of exogenously introduced prostaglandins such as those of the F, E and A series, and to maintain adequate levels of endogenously produced prostaglandins. The compounds of this invention are additionally useful in the treatment of gastric ulcers and may be employed for that purpose in a manner similar to carbenoxolone.

A compound mixture of compounds of formula I including their pharmaceutically acceptable salts can be administered orally or parenterally to various mammalian species in amounts ranging from about 10 to about 100 mg./kg./day divided into one or more doses for the pharmaceutical purpose set forth above. The compounds are formulated with an inert carrier according to conventional pharmaceutical practice. For example in the form of tablets, capsules, or an injectable solution.

EXAMPLE 1

4-[2-(2-Chlorophenyl)ethyl]-1,2,3,6-tetrahydro-1-(2-propenyl)-pyridine, hydrochloride (1:1)

(a) 4-[2-(2-Chlorophenyl)ethyl]pyridine 14.1 g. (0.1 mole) of 2-chlorobenzaldehyde and 9.4 g. (0.1 mole) or 4-methylpyridine are refluxed for six hours in 40ml. of acetic anhydride. The reaction mixture is concentrated in vacuo and then dissolved in 200 ml. of chloroform. The chloroform solution is washed with aqueous sodium bicarbonate, dried with $MgSO_4$, filtered and concentrated in vacuo. The oily residue is dissolved in isopropanol and treated with HCl in isopropanol until acidic. The crystalline hydrochloride salt is filtered, dissolved in 150 ml. of water and neutralized with aqueous sodium bicarbonate. The product is extracted with chloroform to yield 12.6 g. of oil 4-[2-(2-chlorophenyl)ethenyl]pyridine.

(b).

4-[2-(2-Chlorophenyl)ethenyl]-1,2,3,6-tetrahydro-1-(2-propenyl)pyridine, hydrochloride (1:1)

16 g. (0.075 mole) of 4-[2-(2-chlorophenyl)ethenyl]-pyridine from part (a) and 10 g. (0.083 mole) of allyl bromide are added to 150 ml. of acetonitrile. This mixture is allowed to stand at 20° C. overnight. Filtration and a washing of the resulting salt with acetonitrile and ether yields 17 g. of crystalline quaternary material.

17 g (0.05 mole) of this quaternary material is reduced with 9 g. of sodium borohydride in 200 ml. of methanol at 35° C. for two hours. Water is added and the product is extracted with benzene, dried (Na$_2$SO$_4$), and evaporated to yield a dark oil. The oil is dissolved in ethyl acetate and treated with HCl in isopropanol. The resulting hydrochloride salt product is filtered, recrystallized from methanol-acetonitrile, and dried in vacuo to yield 7.0 g. of 4-[2-(2-chlorophenyl)ethenyl]-1,2,3,6-tetrahydro-1-(2-propenyl)pyridine, hydrochloride (1:1); m.p. 234°–236°.

EXAMPLE 2

4-[2-(2-Methoxyphenyl)ethenyl]-1,2,3,6-tetrahydro-1-(2-propenyl)pyridine, hydrochloride (1:1)

(a) 4-[2-(2-Methoxyphenyl)ethenyl] pyridine

A mixture of 96 g. (0.7 mole) of 2-methoxybenzaldehyde and 66 g. (0.71 mole) of 4-methylpyridine in 200 ml. of acetic anhydride is refluxed for 18 hours under nitrogen and evaporated in vacuo to an oil. This residue is taken up in 5% HCl, extracted with ether, basified with 10% sodium hydroxide, extracted with dichloromethane, dried (potassium carbonate), and evaporated to yield 140 g. of crude 4-[2-(2-methoxyphenyl)ethenyl]pyridine as a dark oil.

(b) 4-[2-(2-Methoxyphenyl)ethenyl]-1,2,3,6-tetrahydro-1-(2-propenyl)pyridine, hydrochloride (1:1)

A mixture of 5.3 g. (0.025 mole) of 4-[2-(2-methoxyphenyl)ethenyl]pyridine from part (a) and 3.0 g. (0.025 mole) of allyl bromide in 50 ml. of acetonitrile is allowed to stand for 3 days at 25° C. to yield 7.5 g. of solid yellow quaternary material.

7.5 g. (0.023 mole) of the quaternary material in 200 ml. of methanol is treated in portions with 3 g. of sodium borohydride with ice-water cooling. The mixture is stirred for one hour, diluted with water, extracted with benzene, dried over potassium carbonate, and evaporated to an oil. A solution of this oil in ethyl acetate is treated with HCl in isopropanol to yield 6 g. of crude salt product. A 2.5 g. sample of the crude material is recrystallized from acetonitrile to yield 1.8 g. of 4-[2-(2-methoxyphenyl)ethenyl]-1,2,3,6-tetrahydro-1-(2-propenyl)pyridine, hydrochloride (1:1); m.p. 193°–196°.

EXAMPLES 3–15

Following the procedure of examples 1 and 2 but employing the styrylpyridine shown in Col. I and the halo substituted alkene shown in Col. II one obtains the final product shown in Col. III.

| Ex. | X | halo | n | R$_1$ | R$_2$ | R$_3$ |
|---|---|---|---|---|---|---|
| 3 | Br | halo | 1 | H | H | H |
| 4 | F | Cl | 2 | H | H | H |
| 5 | Cl | Br | 3 | H | H | H |
| 6 | OC$_2$H$_5$ | Br | 1 | CH$_3$ | H | CH$_3$ |
| 7 | n-OC$_3$H$_7$ | Br | 2 | H | H | CH$_3$ |
| 8 | t-OC$_4$H$_9$ | Br | 1 | CH$_3$ | CH$_3$ | CH$_3$ |
| 9 | —OCH$_3$ | Cl | 3 | CH$_3$ | H | H |
| 10 | i-OC$_3$H$_7$ | Br | 1 | H | H | H |
| 11 | Cl | Br | 2 | H | H | H |
| 12 | Cl | Br | 1 | CH$_3$ | H | H |
| 13 | Cl | Br | 1 | CH$_3$ | CH$_3$ | H |
| 14 | Cl | Br | 2 | H | H | CH$_3$ |
| 15 | Cl | Br | 3 | H | H | H |

EXAMPLE 16

4-[2-(2-Methoxyphenyl)ethenyl]-1,2,3,6-tertahydro-1-(2-propynyl)pyridine, hydrochloride (1:1)

(a) 1-Benzyl-4-[2-(2-Methoxyphenyl)ethenyl]-1,2,3,6-tetrahydropyridine 44.7 g. (0.21 mole) of 4-[2-(2-methoxyphenyl)ethenyl]pyridine and 37.6 g. (0.22 mole) of benzylbromide are heated in 200 ml. of acetonitrile on a steam cone for five hours. The resulting quaternary salt is filtered and washed with ethyl acetate to yield 72.5 g.

This quaternary material is dissolved in 1 liter of methanol and 0.4 liters of water. 10 g. of sodium borohydride are added portionwise at 35°–40° C. The mixture is stirred for an additional two hours, concentrated in vacuo to about 1 liter, and extracted with two 400 ml. portions of chloroform. The chloroform extracts are dried with MgSO$_4$, filtered, and concentrated in vacuo to yield 36 g. of 1-benzyl-4-[2-(2-methoxyphenyl)ethenyl]-1,2,3,6-tetrahydropyridine.

(b) 1,2,3,6-Tetrahydro-4-[2-(2-methoxyphenyl)ethenyl]-pyridine

The 1-benzyl product from part (a) is dissolved in 500 ml. of anhydrous toluene. The mixture is cooled to 5° C. and 26.6 g. (0.125 mole) of trichloroethyl chloroformate are added dropwise. Afterward, the reaction mixture is refluxed for four hours. This solution is then cooled, washed sequentially with 100 ml. of 10% HCl, 100 ml. of water, 100 ml. of 10% NaOH, and finally with 100 ml. of saturated aqueous NaCl. The toluene solution is dried with MgSO$_4$, filtered, and concentrated in vacuo to yield 43.5 g. of 1- [[(2-trichloroethyl)oxy]carbonyl]-1,2,3,6-tetrahydro-4-[2-(2-methoxyphenyl)ethenyl]pyridine as an oil.

The above product is dissolved in 450 ml. of glacial acetic acid. While stirring vigorously, 58 g. of zinc dust is added in small portions and the reaction mixture is stirred for six hours. The solution is filtered and concentrated in vacuo. The residual oil is washed with ether.

The ether insolubles are heated on a steam cone with 400 ml. of 10% NaOH for one hour and the product is extracted with 500 ml. of chloroform. The chloroform extract is dried (MgSO4), filtered, and concentrated in vacuo to yield (11.1 g. of crystalline 1,2,3,6-tetrahydro-4-[2-2-methoxyphenyl)ethenyl]pyridine.

(c)
4-[2-(2-Methoxyphenyl)ethenyl]-1,2,3,6-tetrahydro-1-(2-propynyl)pyridine, hydrochloride (1:1)

A mixture of 4.3 g. (0.02 mole) of the product from part (b), 2 g. (0.02 mole) of triethylamine, and 2.4 g. (0.02 mole) of propargyl bromide in 50 ml. of benzene is heated at 60° C. for four hours under nitrogen and then stripped to a slurry. The residue is taken up in water and ether, the organic containing layer is separated and dried over sodium carbonate. Evaporation yields the free base as an oil which is treated with HCl in isopropanol. Recrystallization from acetonitrile yields 4-[2-(2-methoxyphenyl)-ethenyl]-1,2,3,6-tetrahydro-1-(2-propynl)pyridine, hydrochloride (1:1).

EXAMPLES 17–28

Following the procedure of example 16 but employing the 1,2,3,6-tetrahydro-4-[2-(2-substituted phenyl)ethenyl]pyridine shown in Col. I and the halo substituted alkine shown in Col. II, one obtains the final product shown in Col. III.

| Col. I. | Col. II. | Col. III. |
|---|---|---|
| 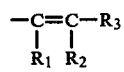 | halo—$(CH_2)_n$—C≡C—$R_4$ | 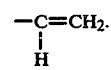 |

| Ex. | X | halo | n | $R_4$ |
|---|---|---|---|---|
| 17 | Cl | Br | 1 | H |
| 18 | Br | Cl | 1 | H |
| 19 | F | Br | 2 | H |
| 20 | $OC_2H_5$ | Br | 1 | $CH_3$ |
| 21 | n-$OCH_3H_7$ | Br | 1 | H |
| 22 | t-$OC_4H_9$ | Br | 2 | H |
| 23 | $OCH_3$ | Br | 3 | H |
| 24 | $OCH_3$ | Br | 2 | $CH_3$ |
| 25 | Cl | Br | 3 | H |
| 26 | Cl | Br | 2 | $CH_3$ |
| 27 | Cl | Br | 2 | H |
| 28 | Cl | Br | 1 | $CH_3$ |

Similarly, by reacting the above starting material shown in Col. I with the halo substituted alkenes shown in Col. II of examples 3–15 according to the procedure of example 16, other compounds within the scope of this invention are obtained.

What is claimed is:

1. A pharmaceutical composition useful for treating gastric ulcers comprising a pharmaceutically acceptable carrier and a compound or mixture of compounds of the formula

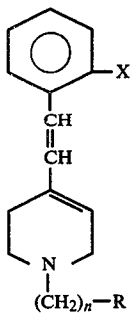

wherein X is straight or branched chain lower alkoxy of 1 to 4 carbons, Cl, Br, or F; R is $$-\underset{R_1}{C}=\underset{R_2}{C}-R_3$$

or —C≡C—$R_4$; $R_1$, $R_2$, $R_3$ and $R_4$ are independently selected from the group consisting of hydrogen and methyl; n is an integer from 1 to 3 provided that when n is 3 at least two of $R_1$, $R_2$ and $R_3$ are hydrogen and $R_4$ is hydrogen, and that when n is 2 at least one of $R_1$, $R_2$ and $R_3$ is hydrogen; and a pharmaceutically acceptable acid addition salt thereof.

2. The composition of claim 1 wherein X is methoxy, ethoxy, Cl, or Br; n is 1 or 2; and $R_1$, $R_2$, $R_3$ and $R_4$ are hydrogen.

3. The composition of claim 1 wherein X is methoxy or Cl; n is 1; and R is $$-\underset{H}{C}=CH_2.$$

4. The composition of claim 3, containing 4-[2-(2-chlorophenyl)ethenyl]-1,2,3,6-tetrahydro-1-(2-propenyl)pyridine, hydrochloride (1:1).

5. The composition of claim 3, containing 4-[2-(2-methoxyphenyl)ethenyl]-1,2,3,6-tetrahydro-1-(2-propenyl)pyridine, hydrochloride (1:1).

6. The method of treating gastric ulcers in a mammalian specie by administering an effective amount of the composition of claim 1.

7. The method of potentiating exogenously introduced prostaglandins by administering to the mammalian specie an effective potentiating amount of a composition of a pharmaceutically acceptable carrier and a compound or mixture of compounds of the formula:

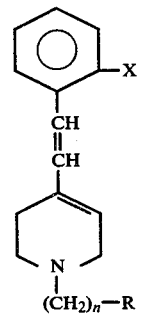

wherein X is straight or branched chain lower alkoxy of 1 to 4 carbons, Cl, Br, or F; R is

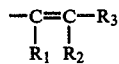

or —C≡C—R$_4$; R$_1$, R$_2$, R$_3$ and R$_4$ are independently selected from the group consisting of hydrogen and methyl; n is an integer from 1 to 3 provided that when n is 3 at least two of R$_1$, R$_2$ and R$_3$ are hydrogen and R$_4$ is hydrogen, and that when n is 2 at least one of R$_1$, R$_2$ and R$_3$ is hydrogen; and a pharmaceutically acceptable acid addition salt thereof.

8. A compound of the formula:

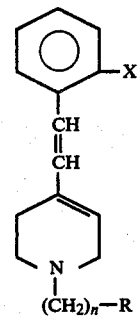

wherein X is straight or branched chain lower alkoxy of 1 to 4 carbons, Cl, Br, or F; R is

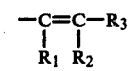

or —C≡C—R$_4$; R$_1$, R$_2$, R$_3$ and R$_4$ are independently selected from the group consisting of hydrogen and methyl; n is an integer from 1 to 3 provided that when n is 3 at least two of R$_1$, R$_2$ and R$_3$ are hydrogen and R$_4$ is hydrogen, and that when n is 2 at least one of R$_1$, R$_2$ and R$_3$ is hydrogen; and a pharmaceutically acceptable acid addition salt thereof.

* * * * *